(12) United States Patent
Yu

(10) Patent No.: US 10,478,561 B2
(45) Date of Patent: Nov. 19, 2019

(54) WIRELESS TRANSMISSION SYSTEM WITH INTEGRATED SENSING CAPABILITY

(71) Applicant: Minhong Yu, Moorpark, CA (US)

(72) Inventor: Minhong Yu, Moorpark, CA (US)

(*) Notice: Subject to any disclaimer, the term of this patent is extended or adjusted under 35 U.S.C. 154(b) by 0 days.

(21) Appl. No.: 16/026,790

(22) Filed: Jul. 3, 2018

(65) Prior Publication Data

US 2019/0038840 A1 Feb. 7, 2019

Related U.S. Application Data

(60) Provisional application No. 62/540,568, filed on Aug. 3, 2017.

(51) Int. Cl.
*H04Q 5/22* (2006.01)
*A61M 5/31* (2006.01)
*H04W 4/38* (2018.01)
*H04W 4/80* (2018.01)

(52) U.S. Cl.
CPC ....... *A61M 5/31* (2013.01); *A61M 2205/3523* (2013.01); *A61M 2205/3584* (2013.01); *A61M 2205/3592* (2013.01); *H04W 4/38* (2018.02); *H04W 4/80* (2018.02)

(58) Field of Classification Search
CPC .. A61M 2205/3523; A61M 2205/3584; A61M 2205/3592; A61M 5/31; A61M 5/31568; A61M 5/5086; H04B 5/0031; H04W 4/38; H04W 4/80
USPC ..................................................... 340/10.33
See application file for complete search history.

(56) References Cited

U.S. PATENT DOCUMENTS

| 4,173,742 | A | 11/1979 | Lehmann |
| 4,794,396 | A | 12/1988 | Pothier |
| 4,987,317 | A | 1/1991 | Pournain et al. |
| 5,451,938 | A | 9/1995 | Brennan |
| 6,030,367 | A | 2/2000 | Balestracci |
| 6,190,362 | B1 | 2/2001 | Balestracci |
| 6,888,509 | B2 | 5/2005 | Atherton |
| 7,098,794 | B2 * | 8/2006 | Lindsay ............. G06K 19/0716 340/539.26 |
| 7,283,054 | B2 | 10/2007 | Girvin et al. |
| 8,002,754 | B2 | 8/2011 | Kawamura |
| 8,282,011 | B1 | 10/2012 | Skoine et al. |
| 9,094,803 | B2 | 7/2015 | Rubin et al. |
| 9,107,565 | B2 | 8/2015 | Jain et al. |

(Continued)

OTHER PUBLICATIONS

European Search Report for European Patent App. No. 18185281.5, dated Feb. 11, 2019, 15 pages.

*Primary Examiner* — Naomi J Small
(74) *Attorney, Agent, or Firm* — Luedeka Neely Group, P.C.

(57) ABSTRACT

A sensor for detecting a change in state of an asset comprising including a transmission antenna operable to transmit a control signal to an external device, control electronics connected to the transmission antenna configured to provide instructions to the transmission antenna to transmit the control signal, and a bypass antenna positioned and configured to prevent the control electronics from providing the instructions to the transmission antenna when the bypass antenna is in an undisturbed position and to permit the control electronics to provide the instructions to the transmission antenna when the bypass antenna is displaced from the undisturbed position.

24 Claims, 10 Drawing Sheets

(56) References Cited

U.S. PATENT DOCUMENTS

| | | |
|---|---|---|
| 9,471,817 B1 * | 10/2016 | Alhazme .......... G06K 19/07345 |
| 9,516,699 B2 | 12/2016 | Okada et al. |
| 9,917,602 B2 | 3/2018 | He |
| 9,917,638 B1 | 3/2018 | Bartur et al. |
| 9,974,091 B2 | 5/2018 | Rubin et al. |
| 2005/0242957 A1 | 11/2005 | Lindsay et al. |
| 2006/0214789 A1 | 9/2006 | Posamentier et al. |
| 2007/0008121 A1 | 1/2007 | Hart |
| 2008/0157975 A1 | 7/2008 | White et al. |
| 2009/0024112 A1 * | 1/2009 | Edwards ................ A61M 5/19 |
| | | 604/890.1 |
| 2009/0128340 A1 | 5/2009 | Masin |
| 2009/0167526 A1 | 7/2009 | Graves et al. |
| 2009/0212950 A1 | 8/2009 | Cheng |
| 2011/0285507 A1 | 11/2011 | Nelson |
| 2012/0113840 A1 | 5/2012 | Pezennec et al. |
| 2012/0207244 A1 * | 8/2012 | Weinerth ............ H03K 17/002 |
| | | 375/316 |
| 2015/0301912 A1 | 10/2015 | Rubin et al. |
| 2016/0030683 A1 * | 2/2016 | Taylor ............... A61M 5/14248 |
| | | 604/151 |
| 2016/0151558 A1 | 6/2016 | Tobescu |
| 2016/0275769 A1 | 9/2016 | McIntosh |

\* cited by examiner

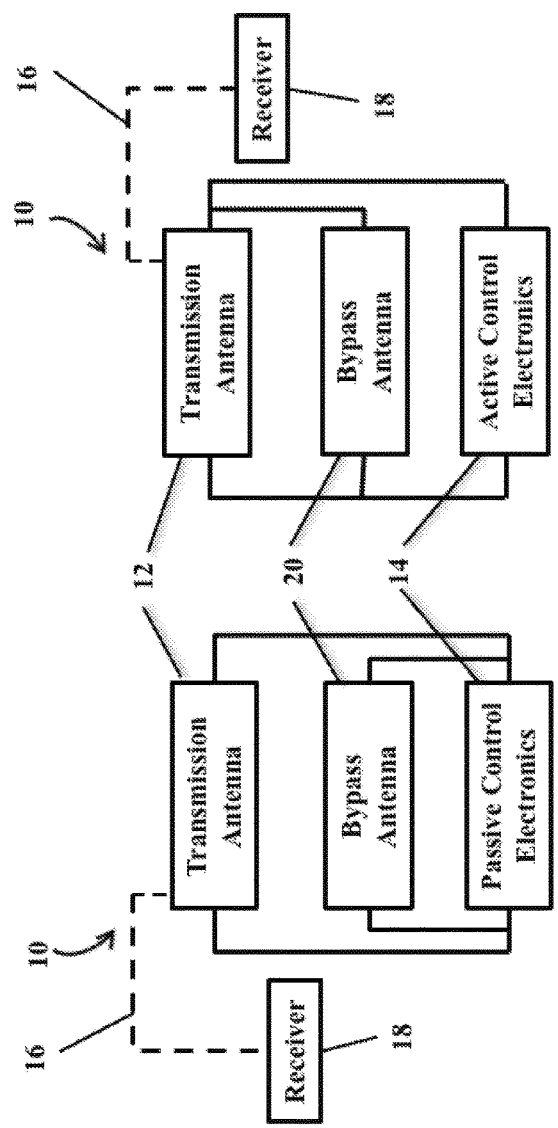
FIG. 1A
FIG. 1B
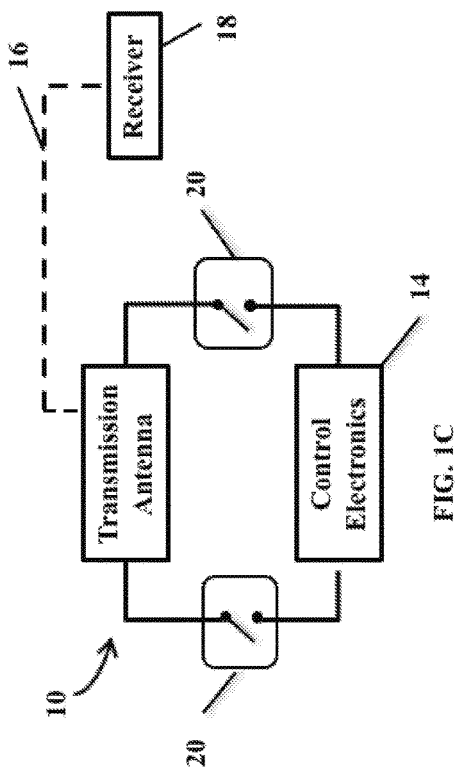
FIG. 1C

WIRELESS TRANSMISSION SYSTEM WITH INTEGRATED SENSING CAPABILITY

CROSS-REFERENCE TO RELATED APPLICATIONS

This application claims priority as a non-provisional to U.S. Provisional Application Ser. No. 62/540,568 filed Aug. 3, 2017, entitled "Adding Sensing Capability to Wireless Transmission Systems Via Integrating Bypass Antenna(s) and/or Sensing Element(s)," the contents of which is incorporated herein by reference.

FIELD

The present disclosure relates generally to a sensor and communication system that can be integrated together to detect an event or change in state of an asset and to transmit such information wirelessly. More particularly, the present disclosure relates to a sensor having a sensor element and communication system integrated together in a low-cost and low-power (or no-power) package that wirelessly transmits a sensor signal only when the sensor detects an event or a change in state of an asset based on displacement of the sensing element.

BACKGROUND

Assets as used herein refers to physical things having parts that can be removed, repositioned, tampered with, displaced, connected to another part of the same asset, etc. (collectively referred to herein as a "change of state"). Detecting an asset's change of state is essential in today's market with wide application. For example, nearly all products ranging from bottled food products to high value electronics rely on tamper evident indicators to provide information on whether the product has been tampered with or otherwise altered. However, such visual cues can be easily missed or avoided. Taking the example of bottled food products, the cap may include a center portion that is popped upward to indicate that the bottle has been opened or otherwise tampered with after the food product was bottled by the manufacturer. Such a tamper indicator is often hard to detect as it requires close examination by the user as well as the user knowing what to look for with the tamper indicator. Similarly, the tamper indicating cap could have been removed altogether and replaced with a different cap that does not indicate tampering.

Similarly, many of today's tamper detection systems are easily replicated. For example, complex tamper indicating labels used by pharmaceutical companies to prevent drug counterfeiting and adulteration often include various hidden features such as Radio Frequency Identification (RFID) tags, holographic images, laser dots, color shifting ink, and self-tear features. The thinking is that it would be very complex for a counterfeiter to duplicate such complex tamper indicators. This may have been the case ten to twenty years ago, but it is now very easy for a counterfeiter to duplicate these types of indicators with the advent of technology by applying a new set of tamper indicating labels to an altered/tampered product.

In addition, all current tamper control systems rely on active inspection (i.e., requiring an individual to physically or visually examine the asset, scan an RFID tag on an asset, etc.) to determine if the product has been tampered with or not. This is very time consuming and heavily dependent on human inspector experience, knowledge, and vigilance.

Detecting an asset's change of state is also particularly helpful in monitoring use of an asset such as with systems for ensuring medication compliance. In ensuring optimal patient treatment, it is essential for patients to comply with a medication regiment prescribed by their health care provider (HCP). Similarly, because no two patients are identical, it is beneficial for HCPs to know whether the patient is in compliance with taking his/her prescribed medication to ensure the best care and medication prescribed for the patient. This information helps HCPs to determine if the medication is working for the patient or a better alternative medication regimen may benefit the patient more than the current regimen.

Similarly, knowing whether a patient has complied with a prescription regimen is necessary to determine the efficacy of new medications in clinical trials. In clinical trials, prefilled syringes are commonly used, and often a new drug will be introduced into the market in prefilled syringes first to be followed by more complex delivery devices such as autoinjectors, capsules, etc. Currently, there are no sensor or electronic systems embedded within prefilled syringes that can provide the HCPs with confirmation of syringe injection usage, which can then be used to correlate medication compliance with treatment efficacy. Today, the HCPs rely on the patients to report medication compliance and on their truthfulness outside of the clinical setting. This reliance on patient truthfulness in taking the prescribed medication regiment can be a significant risk in clinical trials, where the investigative new drug's efficacy, benefits and other results depend heavily on the patients' compliance with the prescribed medication regiment.

While some prior art systems utilize physical and electronics journals and reminder systems to assist and keep track of patient medication compliance, these systems are passive and depend on patient truthfulness and compliance. As such, they are believed to be only marginally effective. A HCP will not be able to tell if, for example, a patient simply filled in their journal right before going in to see their HCP to show compliance despite the patient having been non-compliant. Similarly, with the electronic reminders, the patient may simply indicate injection to silence the alarms without actually injecting the medication.

As such, there exists a need for a system to capture actual asset usage as it occurs and to transmit such information wirelessly (such as to ensure patient compliance and allow the HCPs to determine the efficacy of the medication in the syringe example problem described above).

What is needed therefor is a sensor having broad application to detect an asset's change in state and transmit such information wirelessly. Further, in order to have broad application, the sensor must be provided in a small, low-cost, and low-power package.

SUMMARY

The above and other needs are met by the present disclosure, which provides in one embodiment a sensor for detecting a change in state of an asset. The sensor includes a transmission antenna operable to transmit a control signal to an external device, control electronics connected to the transmission antenna configured to provide instructions to the transmission antenna to transmit the control signal, and a bypass antenna positioned and configured to prevent the control electronics from providing the instructions to the transmission antenna when the bypass antenna is in an undisturbed position and to permit the control electronics to provide the instructions to the transmission antenna when the bypass antenna is displaced from the undisturbed position.

According to certain embodiments, the control electronics is a radio frequency identification (RFID) chip. In some embodiments, the RFID chip is passive such that the control electronics and transmission antenna are configured to transmit the control signal when both the bypass antenna is displaced and the sensor is interrogated by an external device. In other embodiments, the RFID chip is active such that the control electronics and transmission antenna are configured to continuously transmit the control signal when the bypass antenna is displaced. According to other embodiments, the control electronics is a Bluetooth™ chip.

According to certain embodiments, the bypass antenna is in parallel connection with the transmission antenna and control electronics when the bypass antenna is in the undisturbed position. According to other embodiments, the bypass antenna is in series connection between the transmission antenna and control electronics, and the bypass antenna includes a switch configured to move from an open position where the bypass antenna is in the undisturbed position to prevent the control electronics from providing the instructions to the transmission antenna to a closed position where the bypass antenna is displaced to permit the control electronics to provide the instructions to the transmission antenna.

According to certain embodiments, the sensor is configured to be secured to the asset and the bypass antenna is positioned and configured to be displaced based on the change in state of the asset. In some embodiments, the asset is a syringe unit having a plunger rod and the change in state includes delivering fluid out of the syringe unit by depressing the plunger rod. In other embodiments, the asset includes a tamper evident label and the change in state includes one of removal and damage to at least a portion of the tamper evident label. In other embodiments, the asset is an insulin needle and the change in state includes attaching the insulin needle to a pen injector.

According to another embodiment of the disclosure, a method of detecting a change in state of an asset includes providing a sensor and connecting a sensor to the asset. The sensor includes a transmission antenna operable to transmit a control signal to an external device, control electronics connected to the transmission antenna configured to provide instructions to the transmission antenna to transmit the control signal, and a bypass antenna configured to prevent the control electronics from providing the instructions to the transmission antenna when the bypass antenna is undisturbed and to permit the control electronics to provide the instructions to the transmission antenna when the bypass antenna is displaced. The sensor is connected to the asset such that the bypass antenna is positioned to be displaced based on the change in state of the asset.

According to certain embodiments, the asset is a syringe unit having a plunger rod and the change in state includes delivering fluid out of the syringe unit by depressing the plunger rod. According to some embodiments, the sensor is integrated into the plunger rod and the connecting step includes connecting the plunger rod to the syringe unit. According to this embodiment, the plunger rod includes a head portion housing having a bypass antenna displacement mechanism and a finger actuated head portion configured to be displaced within the head portion housing when the plunger rod is depressed. The bypass antenna is positioned and configured within the head portion housing to be displaced when a least a portion of the finger actuated head portion traverses the bypass antenna displacement mechanism.

According to other embodiments, the asset includes a tamper evident label secured to the asset and the change in state includes one of removal and damage to at least a portion of the tamper evident label. In some embodiments, the transmission antenna and control electronics are embedded in the tamper evident label and the bypass antenna is secured in part to the asset and to the tamper evident label such that the bypass antenna is displaced when at least a portion of the tamper evident label is removed from the asset.

According to certain embodiments, the asset includes a first part configured to engage a second part and the change of state includes the first part engaging the second part. In some embodiments, the sensor is integrated into one of the first part and the second part such that the bypass antenna is positioned and configured to be displaced when the first part engages the second part.

According to certain embodiments, the asset includes a movable part and the connecting step includes permanently connecting the sensor to the asset such that the bypass antenna is positioned to be displaced upon a specific motion of the movable part.

According to certain embodiments, the asset includes an intended motion of use and the bypass antenna is positioned to be displaced upon the asset being moved according to the intended motion.

BRIEF DESCRIPTION OF THE DRAWINGS

Further advantages of the invention are apparent by reference to the detailed description when considered in conjunction with the figures, which are not to scale so as to more clearly show the details, wherein like reference numbers indicate like elements throughout the several views, and wherein:

FIGS. 1A-1C are circuit diagrams of a sensor according to various embodiments of the disclosure;

DETAILED DESCRIPTION

Figure 2:
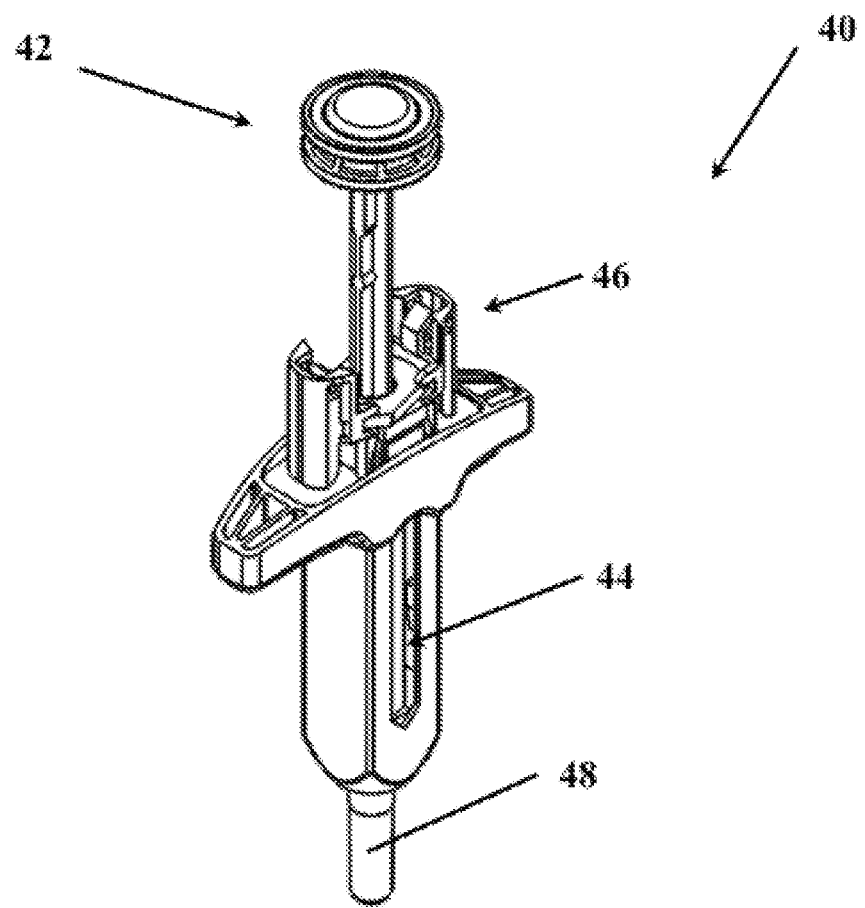
FIG. 2 is a perspective view of a prefilled syringe having a plunger rod incorporating a sensor according to one embodiment of the disclosure.

Referring to FIGS. 1A-1C, the present disclosure provides a sensor 10 in the form of a wireless transmission system having a transmission antenna 12 and control electronics 14. In preferred embodiments, the control electronics 14 is an RFID integrated circuit chip/tag or a Bluetooth® integrated circuit chip/tag as known in the art. The transmission antenna 12 operates to send a control signal (such as a Bluetooth signal when the control electronics 14 is a Bluetooth® integrated circuit chip or a RF signal when the control electronics 14 is an RFID integrated circuit chip) via a wireless communication pathway 16 to an external device/receiver 18 based on instructions from the control electronics 14. The external device 18 may be a standard computer, mobile device such as a smartphone or tablet, RFID reader, or any other device capable of receiving the control signal.

Continuing to refer to FIGS. 1A-1C, the sensor 10 further includes one or more bypass antennas 20 that are configured to prevent the sensor 10 with associated transmission antenna 12 from transmitting the control signal. In other words, sensor 10 is preferably a wireless transmission system that is only activated by displacing, severing, moving, breaking, etc. (hereinafter collectively referred to as displacing, displaced, and/or displacement) any bypass antennas 20 that are preventing transmission of the control signal by the transmission antenna 12. Accordingly, the one or more bypass antennas 20 function as a sensing element in that they activate the wireless transmission system when the one or more bypass antennas 20 are displaced from an undisturbed position to a displaced position. As should be understood, the bypass antenna 20 may take numerous forms such as a wire, switch, etc. so long as functions to suppress the wireless transmission system from sending the control signal until the bypass antenna 20 is displaced.

Referring specifically to FIGS. 1A and 1B, the one or more bypass antennas 20 are preferably in parallel with the transmission antenna 12 and control electronics 14. FIG. 1A depicts one example configuration where the bypass antenna 20 is in parallel with the transmission antenna and the control electronics 14 is "passive." Control electronics 14 of FIG. 1A is referred to as "passive" because it does not include a power source and is only able to transmit the control signal when both the bypass antenna 20 is displaced and sensor 10 is interrogated by an external device 18 having an appropriate interrogator for the passive control electronics 14. For example, a passive RFID chip may be used for the control electronics 14 such that the control electronics 14 are non-operational until the chip is interrogated by an RFID reader. Alternatively, referring to FIG. 1B, the control electronics 14 may be "active" in that sensor continuously transmits (i.e., without the need of an interrogator) the control signal to external device 18 when the bypass antenna 20 is displaced.

Referring to FIG. 1C, according to another embodiment of the disclosure, the bypass antenna 20 may also be in series communication with the transmission antenna 12 and control electronics 14. For example, in the case of a switch being used as the bypass antenna 20, one or more switches 20 are positioned between the transmission antenna 12 and control electronics 14. Displacement of the one or more switches could be in the form of moving the switches from an open position, which prevents connection between the transmission antenna 12 and control electronics 14, to a closed position, which connects the transmission antenna 12 to the control electronics 14 and allows the transmission antenna 12 to send a control signal via communication pathway 16 to the external device/receiver 18.

As should be understood, the sensor 10 of the present disclosure as exemplified in the embodiments of FIGS. 1A-1C, can be utilized in numerous applications where there is a need or desire to detect an asset's change of state including, without limitation, within a tamper/security label, as part of a product's packaging, or within a syringe plunger rod. While the syringe plunger rod embodiment is described in detail below, it should be understood that a similar system could be incorporated into other assets within the teachings of the present disclosure and with similar advantages.

Referring to FIGS. 2-10, a syringe unit 40 having a plunger rod 42, syringe 44, and safety device 46 is exemplified. In preferred embodiments, the syringe unit 40 is preferably a pre-filled syringe with a sheath/needle shield 48 at its distal end and covering the needle (not shown). The safety device 46 is preferably a syringe anti-needle stick safety device such as a BD UltraSafe Passive™ Needle Guard system or a Nemera™ passive safety device.

Figure 3:
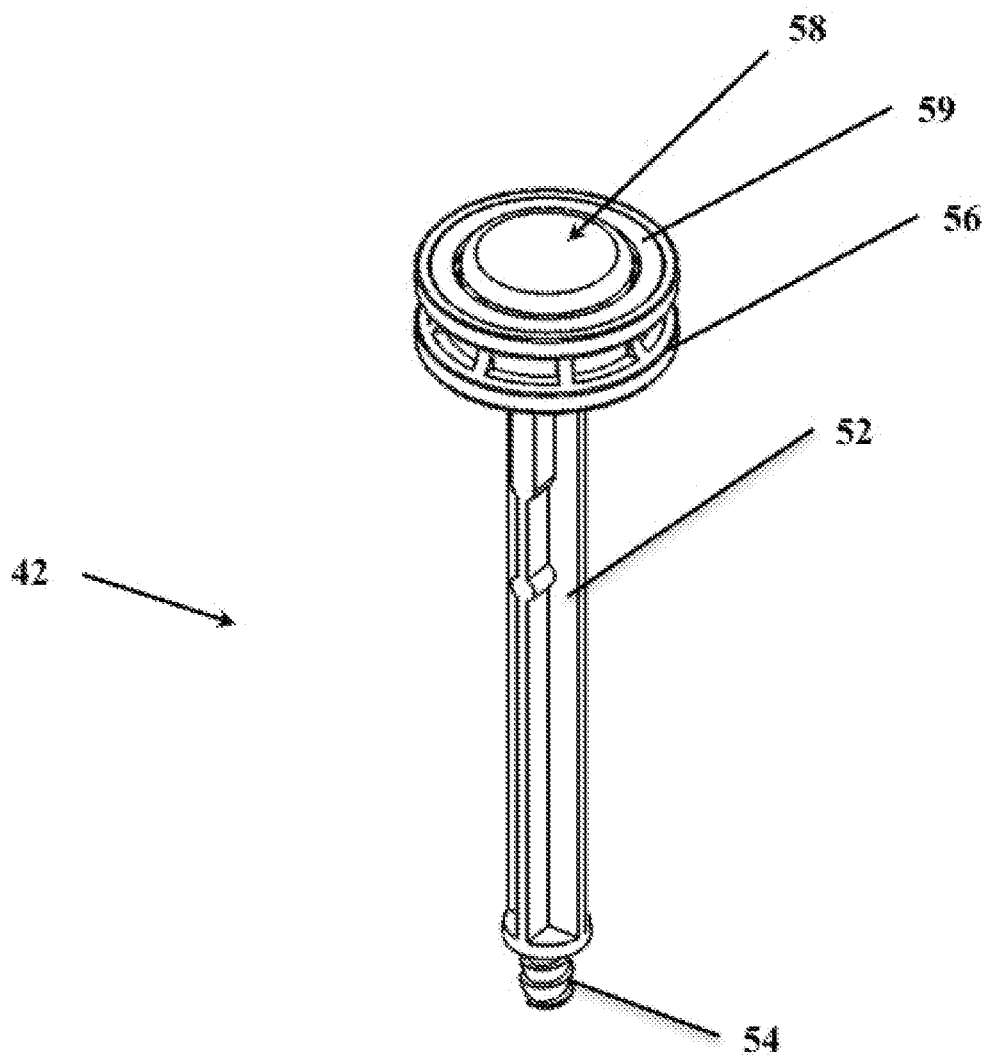
FIG. 3 is a perspective view of the plunger rod of FIG. 2.
Figure 4:
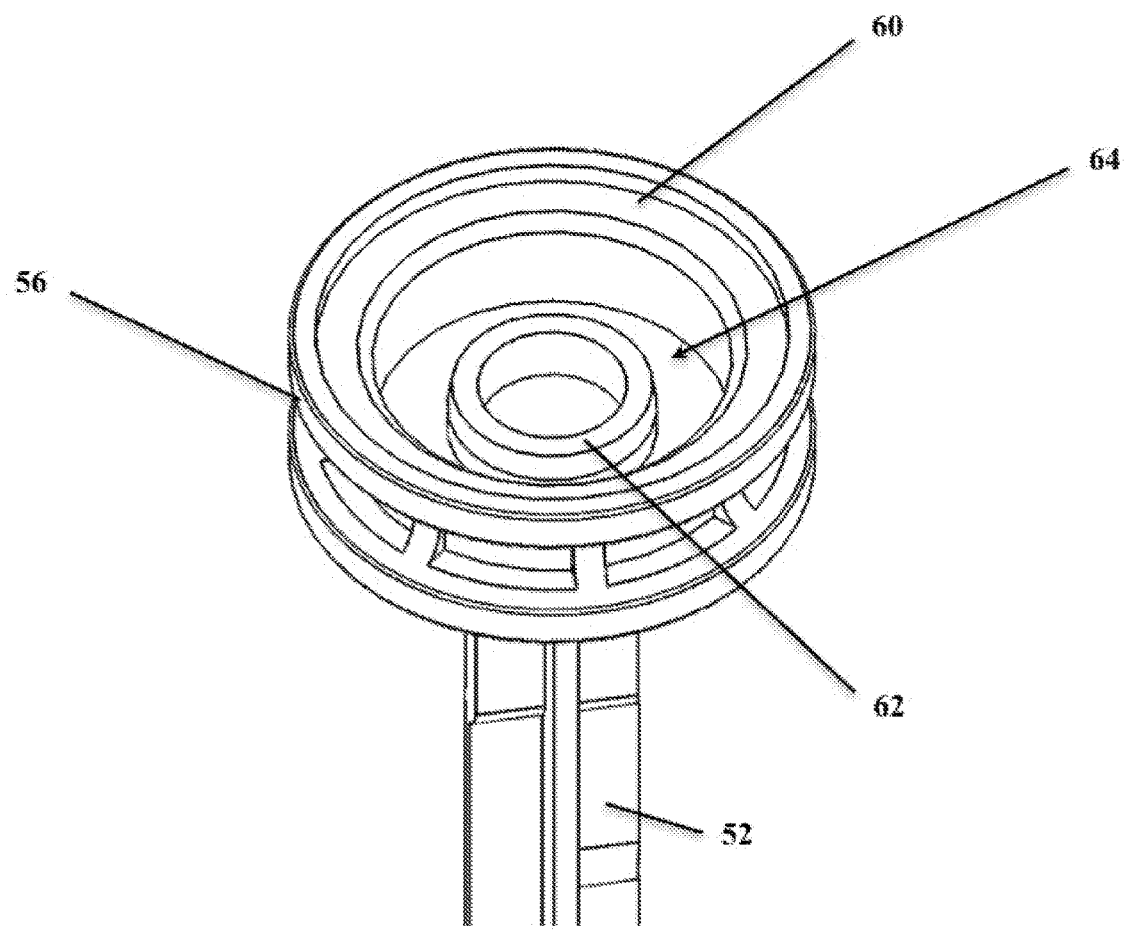
FIG. 4 is an overhead perspective view of the plunger rod of FIG. 3 including an internal view of the head portion housing according to one embodiment of the disclosure.

Referring specifically to FIG. 3, the plunger rod 42 includes a plunger rod shaft 52, a piston engaging member 54 at the distal end of the shaft 52, and a head portion housing 56 at the proximal end of the shaft 52. The piston engaging member 54 is dimensioned and configured to engage a plunger within the syringe 44 to push the plunger in the distal direction to expel the medication/fluid content out of the syringe 44 and through the needle as known in the art. According to this embodiment, the head portion housing 56 includes a finger actuated head portion 58 connected to the top surface of the housing 56 using housing interface member 59 preferably in the form of a connection ring. The housing interface member 59 may be connected to the top surface of housing 56 using a myriad of methods such as adhesive, ultrasonic welding, tight fit, slap fit in place, etc.

The finger actuated head portion 58 is configured to be displaceable within the head portion housing 56 to displace the head portion 58 from the interface member 59. In this regard, referring to FIG. 4, the head portion housing 56 of plunger rod 42 preferably includes an internal collar 60 for receiving the interface member 59. A bypass antenna displacement mechanism 62 is positioned within the housing 56 preferably adjacent a bottom surface of the housing 56. When the connection ring 59 is secured to the internal collar 60, the finger actuated head portion 58 includes a resting (i.e., non-actuated) position where it is positioned above the bypass antenna displacement mechanism 62 with internal space 64 between the bypass antenna displacement mechanism 62 and finger actuated head portion 58.

Figure 5:
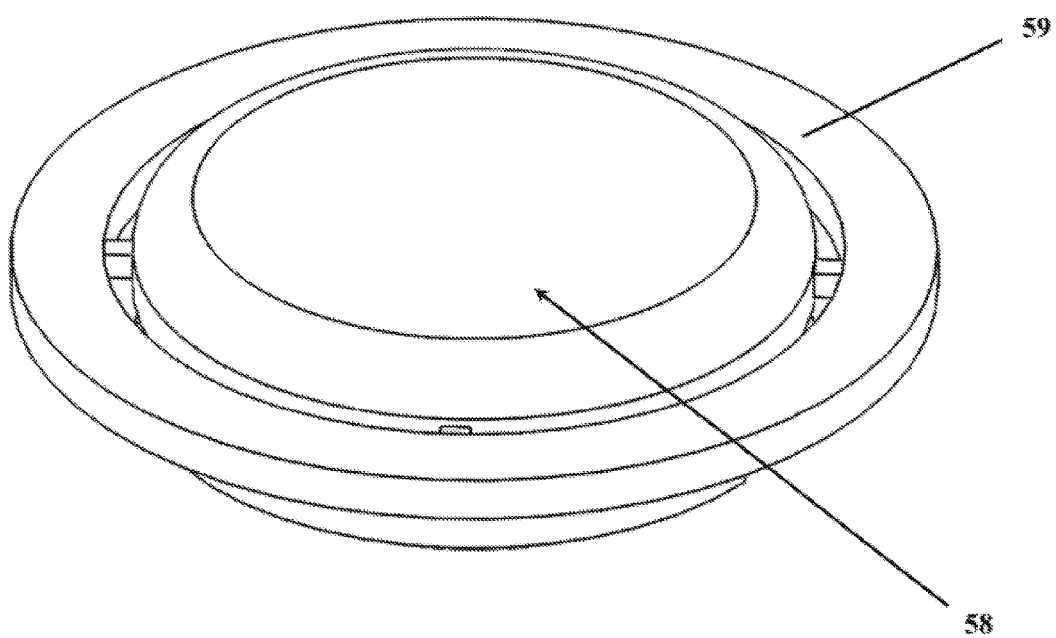
FIG. 5 is a perspective view of a finger actuated head portion of the plunger rod of FIG. 3 connected to an interface member according to one embodiment of the disclosure.
Figure 6:
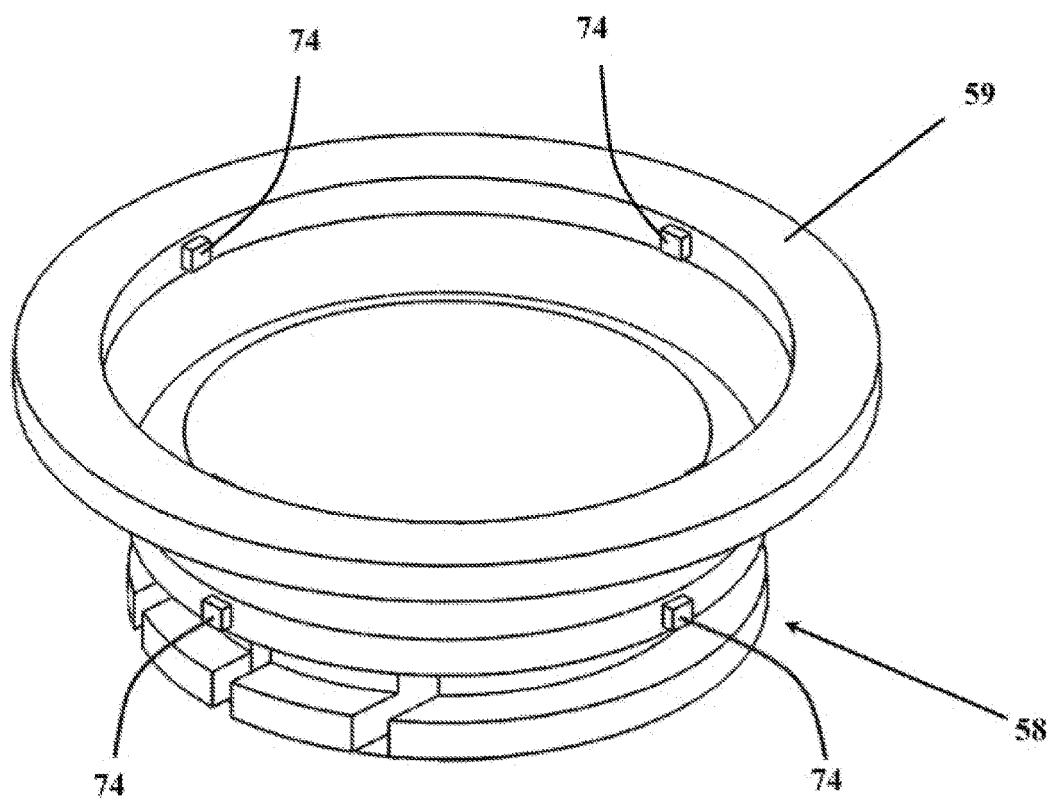
FIG. 6 is a top perspective view of a finger actuated head portion of the plunger rod of FIG. 3 disconnected from the interface member according to one embodiment of the disclosure.

As noted above, referring to FIGS. 5-6, the finger actuated head portion 58 is able to be displaced with respect to interface member 59, which results in the finger actuated head portion 58 being displaced within the head portion housing 56. Referring to FIG. 5, the finger actuated head portion 58 is shown connected to interface member 59. However, referring to FIG. 6, the head portion 58 is configured to be disconnected with respect to interface member 59 when the finger actuated head portion 58 is depressed (i.e., pushed down into the internal space 64 shown in FIG. 4).

Figure 7:
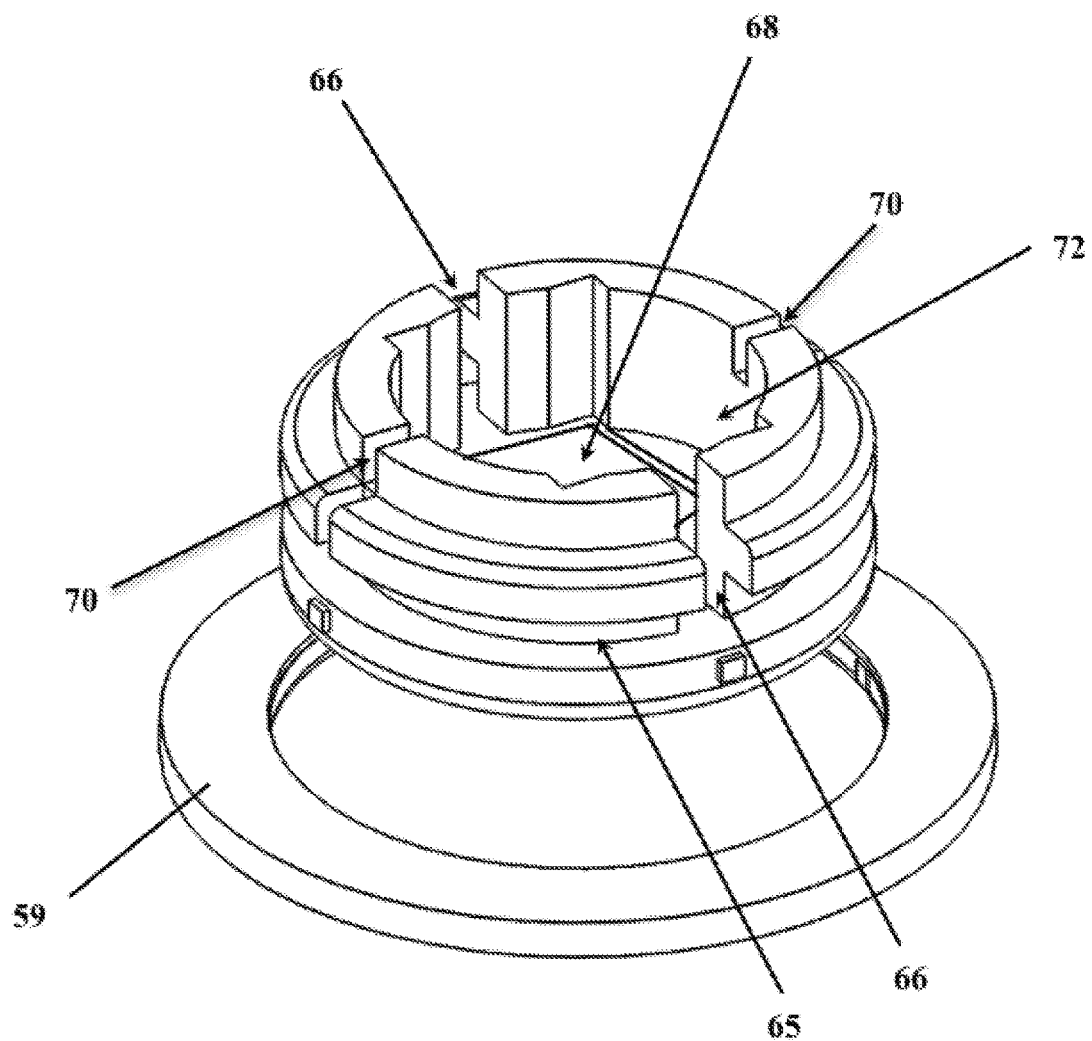
FIG. 7 is bottom perspective view of the finger actuated head portion of FIG. 6 disconnected from the interface member according to one embodiment of the disclosure.
Figure 8:
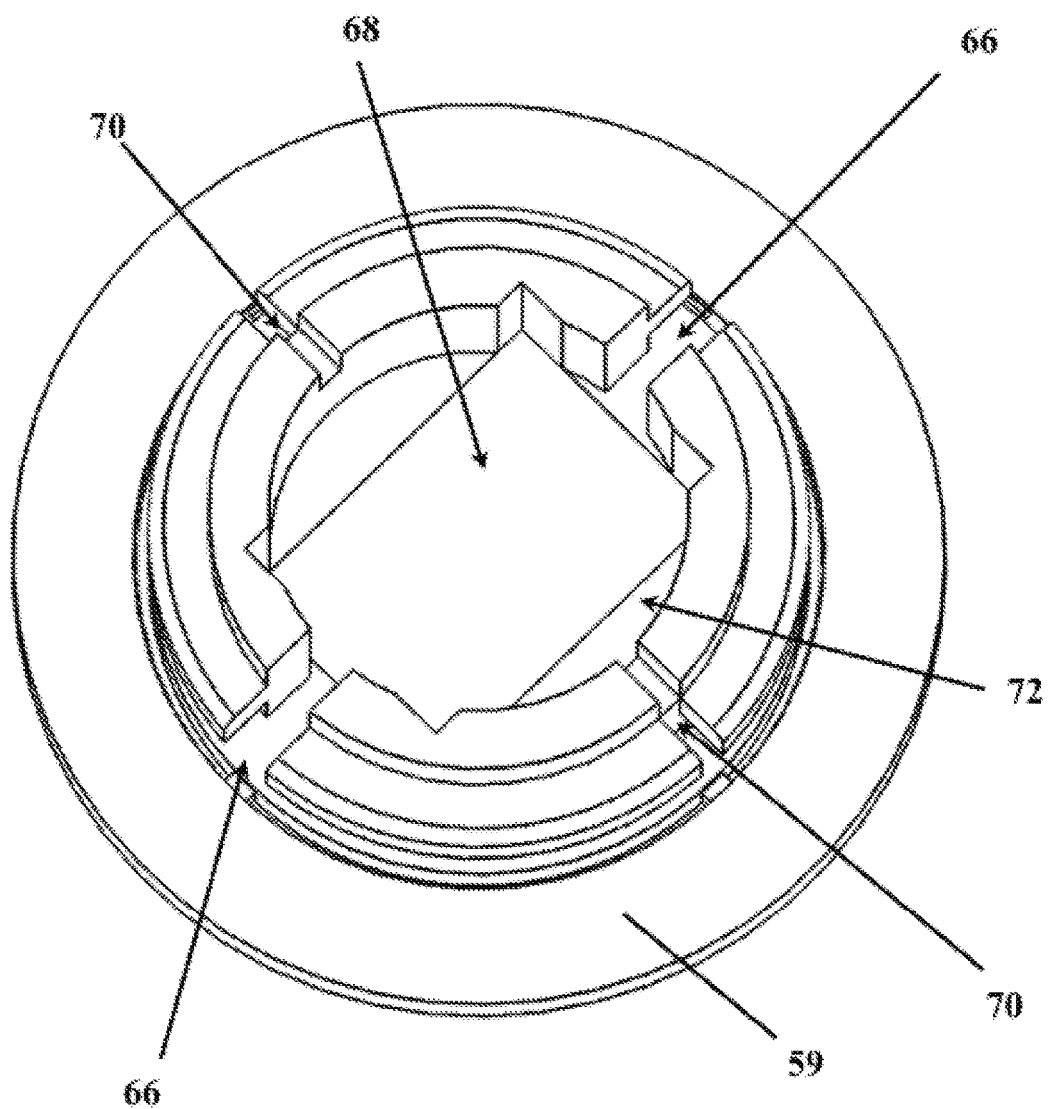
FIG. 8 is a second bottom perspective view of the finger actuated head portion disconnected from the interface member as also depicted in FIG. 7.

Referring to FIGS. 7-8, the finger actuated head portion 58 of this embodiment preferably includes antenna holder 65 (e.g., area in which wiring can be wrapped around the finger actuated head portion 58), transmission antenna slots 66 for receiving transmission antenna 12, control electronics holder 68 for receiving control electronics 14 (e.g., receiving a RF/NFC/Bluetooth wireless communication chip), bypass antenna slots 70 for receiving a bypass antenna 20 (e.g., stretching a wire across slots 70), and internal space 72 to allow for displacement of the bypass antenna 20 from the transmission antenna 12 and control electronics 14 when the finger actuated head portion 58 is displaced with respect to interface member 59.

According to this embodiment, the transmission antenna slots 66 allow the transmission antenna 12 to be attached to chip leads on the control electronics 14. The transmission antenna slots 66 may also be used to attach the bypass antenna 20 to the same chip leads on the control electronics 14 in parallel with the transmission antenna 12. Alternately, additional slots may be provided specifically for connecting the bypass antenna 20. As shown best in FIG. 8, the transmission antenna slots 66 preferably include an internal surface that is in substantially planar alignment with the surface of the control electronics holder 68. On the other hand, the internal surfaces of the bypass antenna slots 70 are preferably raised with respect to the control electronics holder 68 (i.e., non-planar alignment).

Figure 9:
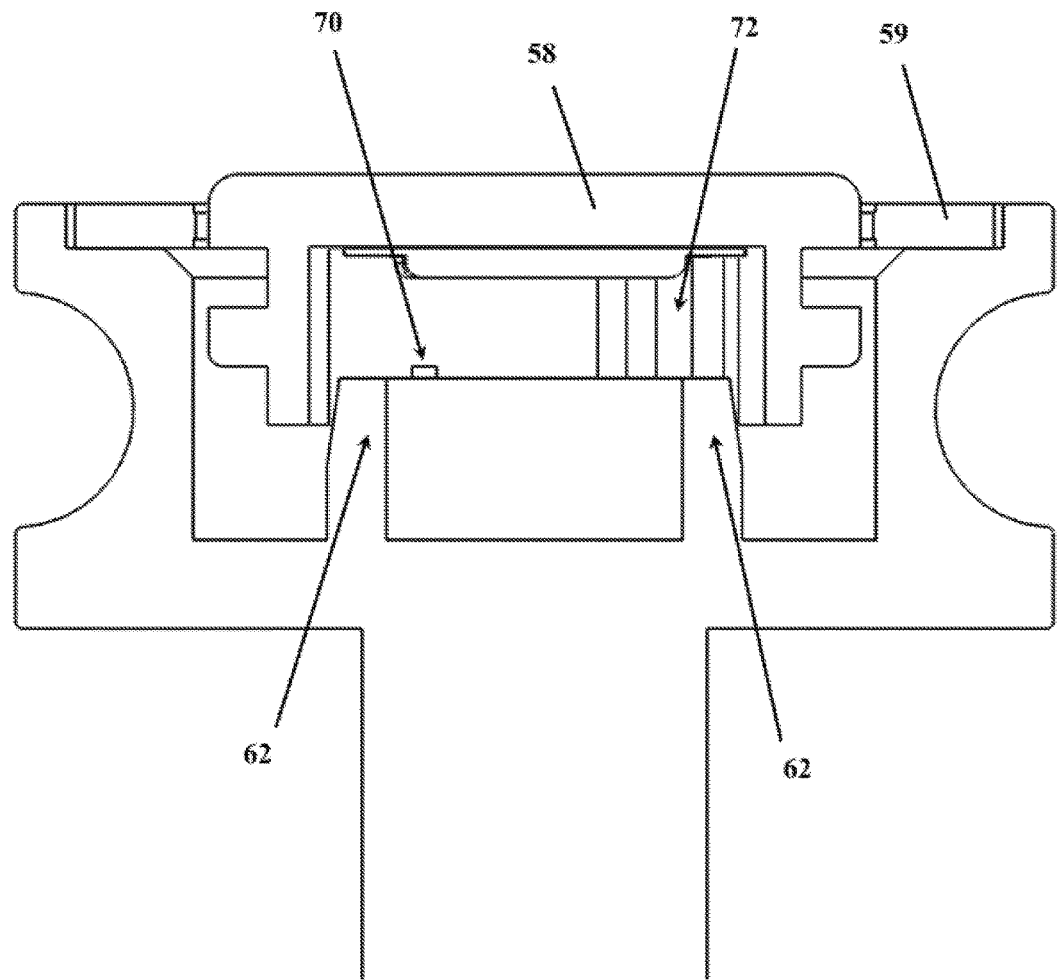
FIG. 9 is a cross-sectional view of a finger actuated head portion in a non-actuated position (i.e., connected to an interface member which is in turn connected to the head portion housing) according to one embodiment of the disclosure.
Figure 10:
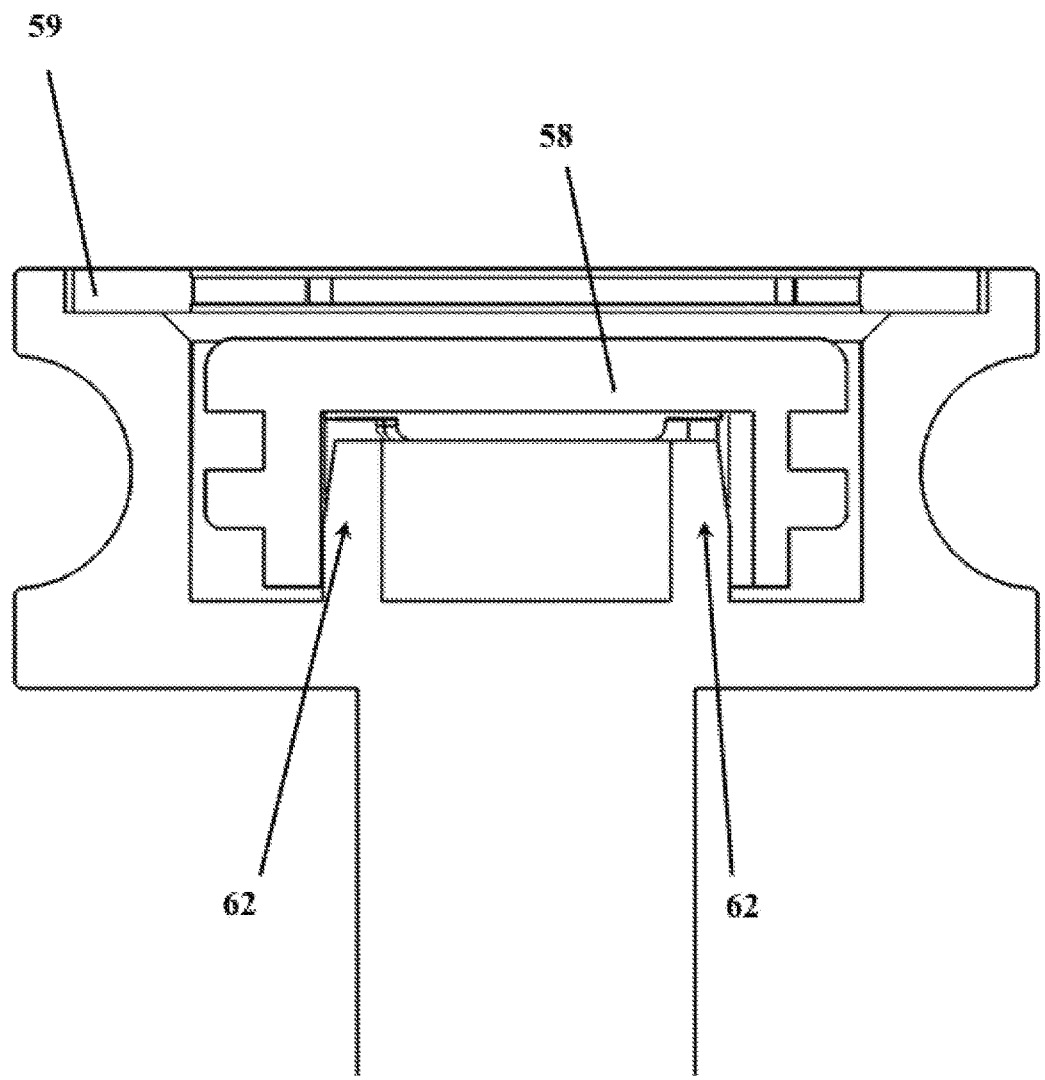
FIG. 10 is a cross-section view of the finger actuated head portion of FIG. 9 in an actuated position (i.e., disconnected from interface member such that bypass antenna would be displaced) according to one embodiment of the disclosure.

In operation, referring to FIGS. 9-10, the finger actuated head portion 58 is configured to move from the non-actuated position (FIG. 9) to the actuated position (FIG. 10) when the finger actuated head portion 58 is depressed. As noted above, in the non-actuated position, the head portion 58 is secured to the interface member 59. However, in the actuated position, the head portion 58 is displaced with respect to the interface member 59 such that the internal space 72 of finger actuated head portion 58 traverses the bypass antenna displacement mechanism 62 within head portion housing 56. When the internal space 72 of finger actuated head portion 58 traverses the bypass antenna displacement mechanism 62, the finger actuated head portion 58 is configured to displace a bypass antenna, which is suspended above the bypass antenna displacement mechanism 62 by being stretched across the bypass antenna slots 70. By displacing the bypass antenna, the transmission antenna 12 and control electronics 14 are enabled and activated to transmit the control signal via communication pathway 16 to external device 18. In other words, according to this embodiment, the wireless transmission system of sensor 10 is activated by removing the bypass antenna 20 when the finger actuated head portion 58 of syringe unit 40 is pressed. The activation of the wireless transmission system of sensor 10 sends a control signal to an external device signaling that the syringe unit 40 has been used to deliver medication/fluid content out of the syringe 44 of syringe unit 40.

It should be understood that sensor 10 as described above may be integrated within the syringe plunger rod 42 in a number of different configurations whereby the bypass antenna 20 is positioned and configured within a finger actuated head portion 58 such that, when the syringe plunger rod is depressed, the bypass antenna 20 is severed/dislodged (i.e., displaced). The force necessary to result in the displacement of the bypass antenna 20 preferably would be a force substantially similar to a force necessary to depress the plunger rod 42 to expel medication from the syringe unit 40. The mechanism for controlling such force could be directly linked to the force necessary to sever/dislodge the bypass antenna 20 or it could be a force necessary to move a bypass antenna holding structure, which would indirectly result in the severing/dislodging of the bypass antenna 20. For example, referring to FIG. 6, the finger actuated head portion 58 may include breakable tabs 74 connected to corresponding breakable tabs 74 on housing interface member 59. Alternately, a weak bridge may be provided between the structures such as tearable adhesive tape. As noted above, the displacement of the bypass antenna 20 enables the transmission antenna 12 and control electronics 14 of sensor 10 to be operational to send a control signal to the external device 18 indicating that the injection from syringe unit 40 has taken place and/or is completed as described above with respect to FIG. 1.

It should also be understood that sensor 10 as described above with respect to syringe unit 40 may integrated within any number of other types of assets. For example, with the integration of a sensing element within a wireless communication system, changes to a product state can be easily monitored such as removal of a label from an asset or undesired movement of a part such as a closure. Enabling the wireless communication system only when a bypass antenna/sensing element is displaced will allow for more robust tamper prevention and at the same time allow for rapid inspection.

With respect to a label embodiment, a typical counterfeiter will simply try to replace a tamper label as known in the art with a new tamper label with a similar wireless communication system. Thus, sensor 10 according to the present disclosure may be provided, for example, with the transmission antenna 12 and control electronics 14 integrated into the label and the bypass antenna 20 connected to both the label and the asset. When the user removes or otherwise damages the label, the bypass antenna 20 is displaced and the sensor 10 is activated. Accordingly, while a counterfeiter thinks that the replacement label is like any other RFID product labels, labels incorporating a sensor according to the present disclosure automatically signals any change of state. In other words, while the counterfeiter believes they have duplicated the exact information as the label on the package, the detection of the wireless transmission signal from a sensor according to the present disclosure provides a rapid alert that the asset has been tampered with or otherwise altered.

According to another exemplary embodiment, and similar to the syringe unit embodiment described above, the asset includes a first part that is configured to engage a second part. Thus, sensor 10 is integrated into one of the first part and second part such that the bypass antenna is positioned and configured to be displaced when the first part engages the second part. For example, an insulin needle is configured to be attached to a pen injector using attachment threading. The sensor 10 may be connected to the insulin needle adjacent to the attachment threading such that the bypass antenna 20 is displaced when the insulin needed is attached to the pen injector, with the resulting control signal indicating that the insulin needle has been used.

In yet another embodiment, the asset may include a movable part and the change of state that is being detected is the movable part having a change in position. Thus, the sensor may be positioned adjacent the movable part or otherwise integrated into the movable part such that the bypass antenna is displaced upon a specific motion of the movable part.

It is also noted that past wireless transmission tamper systems using RFID interrogators are configured to look for the lack of a wireless signal to signify the packaging or product has been tampered with. This takes a significant amount of time and energy. Integrating sensor capability within the wireless communication system allows the inspector to look for the presence of wireless signal, which allows for much more efficient and quicker inspection and saves batter power.

The foregoing description of preferred embodiments for this disclosure has been presented for purposes of illustration and description. It is not intended to be exhaustive or to limit the disclosure to the precise form disclosed. Obvious modifications or variations are possible in light of the above teachings. The embodiments are chosen and described in an effort to provide the best illustrations of the principles of the disclosure and its practical application, and to thereby enable one of ordinary skill in the art to utilize the disclosure in various embodiments and with various modifications as are suited to the particular use contemplated. All such modifications and variations are within the scope of the invention as determined by the appended claims when interpreted in accordance with the breadth to which they are fairly, legally, and equitably entitled.

What is claimed is:

1. A sensor for detecting a change in state of an asset comprising:
 a wireless transmission system configured to transmit a control signal to an external device, the wireless transmission system including:
  a transmission antenna operable to transmit the control signal to the external device,
  control electronics including at least one of a radio frequency identification (RFID) chip and a Bluetooth™ chip in circuit with the transmission antenna configured to provide the control signal to the transmission antenna for transmission to the external device, and
  a sensing element including a bypass antenna operable to move from an undisturbed position to a displaced position, the bypass antenna being in parallel with the transmission antenna and the at least one of the RFID chip and the Bluetooth™ chip when in the undisturbed position to suppress the control signal for preventing the wireless transmission system from transmitting the control signal to the external device, and the bypass antenna operable to permit the control signal to be received by the transmission antenna for transmitting the control signal to the external device when the bypass antenna is displaced from the undisturbed position.

2. The sensor of claim 1 wherein the control electronics includes the RFID chip, the RFID chip being passive such that the transmission antenna transmits the control signal when both the bypass antenna is displaced and the sensor is interrogated by an interrogator as a result of the bypass antenna failing to suppress the control signal provided by the RFID chip to the transmission antenna.

3. The sensor of claim 1 wherein the control electronics includes the RFID chip, the RFID chip being active such that the transmission antenna to continuously transmits the control signal when the bypass antenna is displaced as a result of the bypass antenna failing to suppress the control signal provided by the RFID chip to the transmission antenna.

4. The sensor of claim 1 wherein the control electronics includes the Bluetooth™ chip, the Bluetooth™ chip being active such that the transmission antenna continuously transmits the control signal when the bypass antenna is displaced as a result of the bypass antenna failing to suppress the control signal provided by the Bluetooth™ chip to the transmission antenna.

5. The sensor of claim 1 wherein the sensor is configured to be secured to the asset and the bypass antenna is positioned and configured to be displaced based on the change in state of the asset.

6. The sensor of claim 5 wherein the asset is a syringe unit having a plunger rod and the change in state includes delivering fluid out of the syringe unit by depressing the plunger rod.

7. The sensor of claim 5 wherein the asset includes a tamper evident label and the change in state includes one of removal and damage to at least a portion of the tamper evident label.

8. The sensor of claim 5 wherein the asset is an insulin needle and the change in state includes attaching the insulin needle to a pen injector.

9. A method of detecting a change in state of an asset, the method comprising:
 providing a sensor including:
  a wireless transmission system configured to transmit a control signal to an external device, the wireless transmission system including:
   a transmission antenna operable to transmit the control signal to the external device,
   control electronics including at least one of a radio frequency identification (RFID) chip and a Bluetooth™ chip in circuit with the transmission antenna and configured to provide the control signal to the transmission antenna for transmission to the external device, and
   a sensing element including a bypass antenna operable to move from an undisturbed position to a displaced position, the bypass antenna being in parallel with the transmission antenna and the at least one of the RFID chip and the Bluetooth chip when in the undisturbed position to suppress the control signal for preventing the wireless transmission system from transmitting the control signal to the external device, and the bypass antenna operable to permit the control signal to be received by the transmission antenna for transmitting the control signal to the external device when the bypass antenna is displaced from the undisturbed position; and
 connecting the sensor to the asset such that the bypass antenna is positioned to be displaced based on the change in state of the asset.

10. The method of claim 9 wherein the asset is a syringe unit having a plunger rod and the change in state includes delivering fluid out of the syringe unit by depressing the plunger rod.

11. The method of claim 10 wherein the sensor is integrated into the plunger rod and the connecting step includes connecting the plunger rod to the syringe unit, the plunger rod including a head portion housing having a bypass antenna displacement mechanism and a finger actuated head portion configured to be displaced within the head portion housing when the plunger rod is depressed, the bypass antenna being positioned and configured within the head portion housing to be displaced when a least a portion of the finger actuated head portion traverses the bypass antenna displacement mechanism.

12. The method of claim 9 wherein the asset includes a tamper evident label secured to the asset and the change in state includes one of removal and damage to at least a portion of the tamper evident label.

13. The method of claim 12 wherein the transmission antenna and the at least one of the RFID chip and the Bluetooth™ chip are embedded in the tamper evident label and the bypass antenna is secured in part to the asset and to the tamper evident label such that the bypass antenna is displaced when at least a portion of the tamper evident label is removed from the asset.

14. The method of claim 9 wherein the control electronics includes the RFID chip the RFID chip being passive such that the transmission antenna transmits the control signal when both the bypass antenna is displaced and the sensor is interrogated by an interrogator as a result of the bypass antenna failing to suppress the control signal provided by the control electronics to the transmission antenna.

15. The method of claim 9 wherein the control electronics includes the Bluetooth™ chip, the Bluetooth™ chip being active such that the transmission antenna continuously transmits the control signal when the bypass antenna is displaced as a result of the bypass antenna failing to suppress the control signal provided by the Bluetooth™ chip to the transmission antenna.

16. The method of claim 9 wherein the asset includes a first part configured to engage a second part and the change of state includes the first part engaging the second part.

17. The method of claim 16 wherein the sensor is integrated into one of the first part and the second part such that the bypass antenna is positioned and configured to be displaced when the first part engages the second part.

18. The method of claim 9 wherein the asset includes a movable part and the connecting step includes permanently connecting the sensor to the asset such that the bypass antenna is positioned to be displaced upon a specific motion of the movable part.

19. The method of claim 9 wherein the asset includes an intended motion of use and the bypass antenna is positioned to be displaced upon the asset being moved according to the intended motion.

20. A sensor for detecting a change in state of an asset comprising:
 a transmission antenna operable to transmit an interrogation response signal to an external device;
 an RFID chip connected in circuit with the transmission antenna, the RFID chip configured to generate the interrogation response signal only in response to receiving an interrogation signal from an interrogator and configured to provide the interrogation response signal to the transmission antenna; and
 a bypass antenna operable to move from an undisturbed position to a displaced position, the bypass antenna being in parallel with the transmission antenna and the RFID chip when in the undisturbed position to suppress the interrogation response signal as it is transmitted from the RFID chip to the transmission antenna for preventing the transmission antenna from transmitting the interrogation response signal to the external device, and the bypass antenna permitting an unsuppressed interrogation response signal to be transmitted from the RFID chip to the transmission antenna when in the displaced position for allowing the transmission antenna to transmit the interrogation response signal to the external device.

21. The sensor of claim 20 wherein the sensor is configured to be secured to the asset and the bypass antenna is positioned and configured to be displaced based on the change in state of the asset.

22. The sensor of claim 21 wherein the asset is a syringe unit having a plunger rod and the change in state includes delivering fluid out of the syringe unit by depressing the plunger rod.

23. The sensor of claim 21 wherein the asset includes a tamper evident label and the change in state includes one of removal and damage to at least a portion of the tamper evident label.

24. The sensor of claim 21 wherein the asset is an insulin needle and the change in state includes attaching the insulin needle to a pen injector.

\* \* \* \* \*